United States Patent [19]

Watson et al.

[11] 4,191,614

[45] Mar. 4, 1980

[54] DISTILLATION APPARATUS

[75] Inventors: James M. Watson; Michael E. Johnson, both of Big Spring, Tex.

[73] Assignee: Cosden Technology, Inc., Big Spring, Tex.

[21] Appl. No.: 662,566

[22] Filed: Mar. 1, 1976

[51] Int. Cl.² ............................................. B01D 1/00
[52] U.S. Cl. .................................... 202/177; 202/173; 203/DIG. 25; 203/9
[58] Field of Search ............................ 203/9, DIG. 25; 202/173, 163, 177, 159; 260/669 A; 261/153

[56] References Cited

U.S. PATENT DOCUMENTS

| | | | |
|---|---|---|---|
| 2,389,793 | 11/1945 | Livingston | 260/669 A |
| 2,407,861 | 9/1946 | Wolk | 203/9 |
| 2,473,203 | 6/1949 | Howe | 203/9 |
| 3,408,264 | 10/1968 | Ward | 203/9 |
| 3,515,647 | 6/1970 | Tassell | 203/49 |
| 3,631,214 | 12/1971 | Engelbrecht | 260/669 |
| 3,904,484 | 9/1975 | King | 260/669 X |

*Primary Examiner*—Hiram H. Bernstein

[57] ABSTRACT

Apparatus for the distillation of styrene from hydrocarbon feedstock incorporating a system for injection of gaseous polymerization inhibitor.

6 Claims, 1 Drawing Figure

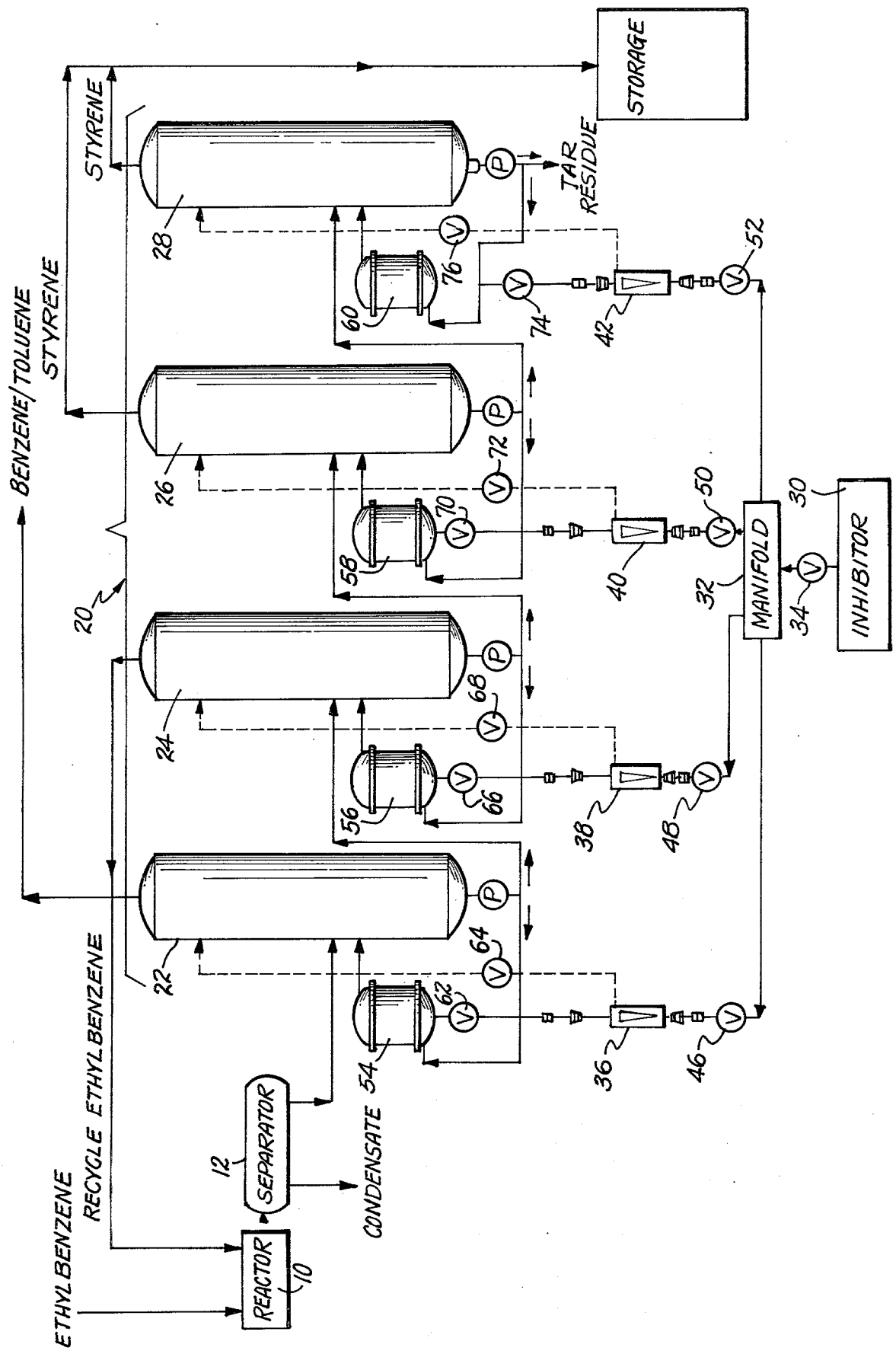

ND_DESCRIPTION
DISTILLATION APPARATUS

BACKGROUND OF THE INVENTION

The present invention relates to apparatus for the distillation of styrene monomer from hydrocarbon feedstocks, wherein polymerization of the styrene product is prevented by injection of a gaseous inhibitor. More particularly, the present invention relates to apparatus for distillation of styrene from ethylbenzene wherein a system is incorporated for injecting nitrogen-based gases as polymerization inhibitors.

DESCRIPTION OF THE PRIOR ART

It is well known in the prior art to produce styrene monomer via various, diverse distillation processes from hydrocarbon feedstocks. For example, it has long been known to subject ethylbenzene to catalytic dehydrogenation followed by fractional distillation to yield styrene. The fractionation serves to separate styrene from other reaction products and to yield a relatively pure product stream freed from such contaminants as tars and/or polymeric materials. Difficulty is encountered, however, since the styrene monomer has a propensity to polymerize under conditions of heat, and particularly those to which the styrene-containing feedstock is exposed in the operation of an efficient distillation process. Therefore, it has become widespread practice to employ various styrene polymerization inhibitors such as sulfur, tertiarybutylcatechol, hydroquinone, certain nitroso compounds, etc. Typically, these polymerization inhibitors are added as liquids at suitable points within the distillation train. See, for example, U.S. Pat. No. 3,515,647.

Recent developments in the field of styrene polymerization inhibitors, especially those effective during the separation and purification of styrene, have provided certain effective gaseous inhibitors. These gaseous inhibitors, most notably nitrogen oxides and derivatives thereof, have proved exceedingly effective in inhibiting the polymerization of styrene monomer during distillation thereof. The degree of efficacy permits introduction of the inhibitors into the distillation system at various, advantageous points and also under differing conditions of operation. Accordingly, the need exists to provide suitable apparatus which may incorporate this new technology into commercial production.

SUMMARY OF THE INVENTION

Therefore, it is a primary object of the present invention to provide an apparatus for the distillation of styrene monomer which incorporates means for injecting gaseous inhibitor to prevent polymerization during the distillation process.

It is another object of the present invention to provide an apparatus capable of yielding commercially significant quantities of pure styrene monomer in a simple, yet highly efficient manner by injecting gaseous, nitrogen-based inhibitors into the distillation train whereby styrene polymerization is precluded.

In accomplishing the foregoing objects there has been provided, according to the present invention, an apparatus for the distillative purification and recovery of styrene monomer from a styrene-containing feedstock, which apparatus includes at least one distillation column for receiving the feedstock, means for introducing the gaseous inhibitor into the column whereby polymerization of the styrene monomer is prevented, and means for recovering said monomer. The gaseous inhibitor is introduced through flow means for controllably admitting the inhibitor to the distillation column.

The single distillation column is adapted for use in conjunction with a crude styrene feedstock. In the event the feedstock is derived from, for example, the catalytic dehydrogenation of ethylbenzene, a plurality of distillation columns is provided. The distillation train is comprised of at least three columns and, peferably, four, each of which has associated therewith a reboiler. Gaseous inhibitor may be injected directly into the reboilers and/or, optionally, into the vapor space of each of the columns. Additionally, when a distillation train is employed, a manifold is provided whereby gaseous inhibitor may be selectively and controllably admitted to each individual column.

Other objects, features and advantages of the invention will become apparent from the detailed description of preferred embodiments which follows, when considered together with the attached sheet of drawings.

BRIEF DESCRIPTION OF THE DRAWINGS

The FIGURE of drawing is a process flow diagram depicting an apparatus according to one preferred embodiment of the present invention.

DETAILED DESCRIPTION OF THE INVENTION

The distillation of styrene monomer has heretofore normally been accomplished under the influence of either liquid or solid polymerization inibitors. To the contrary, the present invention is directed to distillation apparatus adapted for utilization of the newly-developed gaseous inhibitor technology by incorporating means into the distillation apparatus for injecting gaseous inhibitor during the distillation process.

Broadly, the present invention pertains to apparatus for inhibiting polymerization of styrene during separation and purification of the monomer. Separation is accomplished by distillation conducted at elevated temperatures and, generally, under reduced pressure, i.e., subatmospheric. The feed to the distillation apparatus is, in some cases, crude styrene, which can be defined as a mixture predominantly composed of styrene, but contaminated with undesirable quantities of non-volatile components, tars and/or polymeric material, which must be separated. It is possible to employ a single fractionating column or a distillation train including a plurality of columns. The number of columns required will vary with the purity of the styrene and the type of impurities contained therein and can readily be determined by those skilled in the art. Regardless, however, of the precise nature of the feed, and hence, the number of columns, the new gaseous inhibitors have been found to effectively preclude polymerization of styrene in the apparatus if means are provided for appropriately introducing the inhibitors thereto.

The FIGURE of drawing diagrammatically depicts an apparatus according to one embodiment of the present invention. In the illustrated apparatus, the feed to the distillation unit is that resulting from the catalytic dehydrogenation of ethylbenzene. Preliminary separation of various constituents is carried out prior to the purification of styrene. Depending upon the purity of the styrene and the nature of its impurities, that portion of the apparatus associated with the initial, separatory treatments may not be required. Accordingly, the FIG- URE of drawing will serve to illustrate either eventuality.

Ethylbenzene is delivered to a reactor 10 wherein it is catalytically dehydrogenated to yield an effluent containing benzene, toluene, unreacted ethylbenzene, styrene, high boiling polymers, and some tar. This effluent is directed to a separator 12, as is conventional in the art, before being routed to a distillation train, generally denoted as 20. The liquid effluent is subjected to a first fractionation in column 22 wherein benzene and toluene are taken overhead. In the event the initial ethylbenzene feed is derived from the alkylation of benzene and ethylene, the overhead fraction of benzene and toluene may be recycled to the associated apparatus. A bottom mixture of ethylbenzene and styrene monomer, along with residue, is recovered and routed to a second column 24, wherein unreacted ethylbenzene is recovered overhead and recycled to reactor 10. Crude styrene is recovered as a bottom product from tower 24 and is directed to a first finish column 26.

The overhead product from column 26 is styrene of high purity which is routed to storage. The apparatus may be limited solely to the first finish column for separation of styrene monomer. However, there is preferably provided a second finish column 28 which receives the bottom product from tower 26, which bottom product is comprised of styrene and some tar residue. Second finish column 28 removes the tar component that yields high purity styrene as an overhead product which is also directed to storage.

During the distillative separation of the styrene monomer from the other, undesirable components, the conditions of heat within distillation train 20 are such that there is a pronounced tendency for polymerization of the styrene. To prevent this highly deleterious result, gaseous inhibitor is injected into the various columns of the distillation train. The gaseous inhibitor is stored in a suitable vessel 30 which communicates with a manifold 32 via regulator 34. From manifold 32, the gaseous inhibitor is routed to each of the columns 22, 24, 26 and 28 through appropriate flow control apparatus. Generally, it has been determined that the distribution of the gaseous inhibitor between the columns 22, 24, 26 and 28 will depend upon the relative temperatures of operation of the columns with the amount increasing with higher temperatures and decreasing with lower temperatures. The optimum amounts may be readily determined by those skilled in the art.

To suitably apportion the requisite quantity of gaseous inhibitor to the appropriate column, there are provided a plurality of rotameters 36, 38, 40 and 42 which provide operative communication between the source of inhibitor 30 and columns 22, 24, 26 and 28, respectively. Valves 46, 48, 50 and 52 are included to permit selective control of the distribution of inhibitor in the event it is desirable to modulate injection thereof to one or more of the columns within the distillation train.

Reboilers 54, 56, 58 and 60 are associated with each of the distillation columns 22, 24, 26, and 28, respectively, as is conventional. Gaseous inhibitor is selectively and controllably admitted to the bottoms of each of the distillation columns through the associated reboiler, precise control of the desired quantity being achieved by appropriate manipulation of the respective rotameters. Should more sophisticated instrumentation than rotameters be desired, electronic mass flow meters and controllers, and the like, are readily available in the market place than may be employed to this end. Regardless of the manner in which flow is controlled and apportioned, the ultimate operating parameters of the distillation train, which will be individually determined via actual trials for each apparatus, will dictate in large part the appropriate quantity of gaseous inhibitor to each column. More importantly, however, the amount of gaseous material to be employed will depend upon the particular inhibitor taking into account its longevity as well as its inhibiting effect. For example, in the case of nitrogen oxide-type inhibitors, it is preferred to maintain a concentration of from between about 100 ppm and about 3,000 ppm, and preferably from about 100 ppm to about 1,000 ppm in the column.

As illustrated in the FIGURE of drawing, there are provided parallel flow paths for injection of gaseous inhibitor into each of the columns within distillation train 20. Viewing column 22 and its associated apparatus as exemplary of each of the remaining columns, it is possible to precisely control the injection of gaseous inhibitor into the column to provide the most efficient operation thereof. Normally, the gaseous inhibitor will be injected into the bottom of column 22 through reboiler 54 by suitably opening and closing valves 62 and 64. An optional point of injection is provided within the vapor space of the column, the flow path therefor being shown in phantom lines. Moreover, it may well be desirable to inject a portion of the gaseous inhibitor into the bottom of column 22 via reboiler 54 and also inject a portion within the vapor space. This is easily accomplished by adusting rotameter 36 to the desired, absolute flow rate and then appropriately setting valves 62 and 64 to yield the desired division of gas. The remaining columns are provided with identical means to selectively and controllably admit any desired quantity of gaseous inhibitor to the column, apportioning same between bottoms and vapor spaces as desired.

Various gaseous inhibitors may be employed for injection within the distillation train. Insofar as the broad thrust of the present invention regards the distillation of styrene, the preferred gaseous inhibitors are nitrogen oxides and derivatives thereof which include, as preferred, $NO, N_2O_3, NO_2$, and $NOCl$. Most favored is NO as this gas has been determined particularly effective in inhibiting the polymerization of styrene during the distillation process. This material may be supplied from a mobile shipping container or by onsight generation. Accordingly, the source of gaseous inhibitor has merely been designated, in general terms, by the reference numeral 40 in the drawing.

While the present invention has now been described in terms of certain preferred embodiments thereof, the skilled artisan will appreciate that yet other modifications, changes, omissions and substitutions may be made without departing from the spirit of the invention. Accordingly, it is intended that the scope of the present invention be limited only by the following claims.

What is claimed is:

1. Apparatus for the distillative purification and recovery of styrene monomer from a styrene-containing feedstock, comprising:
   (a) at least one distillation column for receiving said feedstock;
   (b) a reboiler operatively associated with each column;
   (c) gas injection means for introducing a gaseous inhibitor into each column;
   (d) gas injection means for introducing a gaseous inhibitor into each reboiler;

(e) a source of gaseous inhibitor in operative communication with each of said gas injection means;

(f) gas flow control means including at least one valve member intermediate said source of gaseous inhibitor and each of said gas injection means for permitting controlled simultaneous apportionment of said gaseous inhibitor between each column and each reboiler, whereby polymerization of said monomer is prevented; and, (g) means to recover said monomer.

2. The apparatus of claim 1, wherein said apparatus comprises a distillation train including at least three columns:

(a) the first of said columns being adapted to remove and collect benzene and toluene as an overhead product and deliver the bottom product of styrene, unreacted ethylbenzene, high boiling polymer, and tar to a second of said columns;

(b) the second of said columns being adapted to remove and recycle said unreacted ethylbenzene as an overhead product and deliver the bottom product of crude styrene to a third of said columns;

(c) the third of said columns being adapted to remove pure styrene monomer and deliver same for collection.

3. The apparatus of claim 2, wherein said gas injecting means includes an inlet for said gaseous inhibitor into the vapor space of each of said columns.

4. The apparatus of claim 2, further comprising:

(a) a fourth column for receiving the bottom product of styrene and tar from said third column, said fourth column being adapted to remove and deliver pure styrene monomer as an overhead product; and (b) a reboiler operatively associated with said fourth column.

5. The apparatus of claim 4, wherein said gas injecting means includes an inlet for gaseous inhibitor into said reboiler for said fourth column.

6. The apparatus of claim 4, wherein said gas injecting means includes an inlet for gaseous inhibitor into the vapor space of said fourth column.

* * * * *